US011331287B2

(12) United States Patent
Bortz

(10) Patent No.: US 11,331,287 B2
(45) Date of Patent: May 17, 2022

(54) IRON SUPPLEMENT

(71) Applicant: Balchem Corporation, New Hampton, NY (US)

(72) Inventor: Jonathan David Bortz, St. Louis, MO (US)

(73) Assignee: Balchem Corporation, New Hampton, NY (US)

( * ) Notice: Subject to any disclaimer, the term of this patent is extended or adjusted under 35 U.S.C. 154(b) by 768 days.

(21) Appl. No.: 14/288,802

(22) Filed: May 28, 2014

(65) Prior Publication Data

US 2014/0364491 A1   Dec. 11, 2014

Related U.S. Application Data

(60) Provisional application No. 61/831,879, filed on Jun. 6, 2013.

(51) Int. Cl.
| | | |
|---|---|---|
| *A61K 31/295* | (2006.01) | |
| *A61K 31/315* | (2006.01) | |
| *A61K 31/16* | (2006.01) | |
| *A61K 45/06* | (2006.01) | |
| *A61K 33/26* | (2006.01) | |
| *A61K 33/30* | (2006.01) | |
| *A61K 9/20* | (2006.01) | |

(52) U.S. Cl.
CPC ............ *A61K 31/16* (2013.01); *A61K 9/2013* (2013.01); *A61K 33/26* (2013.01); *A61K 33/30* (2013.01); *A61K 45/06* (2013.01)

(58) Field of Classification Search
CPC .................................. A61P 39/04; A61P 3/02
See application file for complete search history.

(56) References Cited

U.S. PATENT DOCUMENTS

| | | | |
|---|---|---|---|
| 5,075,469 A | 12/1991 | Chevion | |
| 5,516,925 A | 5/1996 | Pedersen et al. | |
| 5,536,507 A * | 7/1996 | Abramowitz | ........ A61K 9/5073 424/479 |
| 6,521,247 B1 * | 2/2003 | deVries | .................... A23L 33/15 424/439 |
| 7,160,855 B2 | 1/2007 | Theil | |
| 8,007,846 B2 | 8/2011 | Thompson et al. | |
| 2008/0193531 A1 | 8/2008 | Hermelin et al. | |
| 2009/0028962 A1 | 1/2009 | Bortz et al. | |
| 2009/0068190 A1 * | 3/2009 | Bortz | ..................... A61K 31/10 424/141.1 |

FOREIGN PATENT DOCUMENTS

| | | |
|---|---|---|
| CN | 1965697 A | 5/2007 |
| CN | 101744120 A | 6/2010 |
| CN | 102318764 A | 1/2012 |
| WO | 2010136839 A1 | 12/2010 |
| WO | WO-2013/044246 A1 | 3/2013 |

OTHER PUBLICATIONS

International Search Report and Written Opinion dated Oct. 1, 2014 issued in PCT application No. PCT/US2014/039738.
"Duet Chewable Tablets" information sheet from Drugs.com, *StuartNatal (Integrity Pharmaceutical)*, (retrieved 2013).
"New OB Complete One" information sheet, *Vertical Pharmaceuticals, Inc.* (revised 2010).
"New OB Complete Petite" information sheet, *Vertical Pharmaceuticals, Inc.* (revised 2012).
Algren, D.A., (undated) "Review of oral iron chelators (Deferiprone and Deferasirox) for the treatment of iron overload in pediatric patients", 18th Expert Committee on the Selection and Use of Essential Medicines (http://www.who.int/selection_medicines/committees/expert/18/applications/iron/en/index.html).
Armelin, M.J.A., et al. (2003) "Effect of chelated mineral supplementation on the absorption of Cu, Fe, K, Mn and Zn in horse hair", *Journal of Radioanalytical and Nuclear Chemistry*, 258(2):449-451.
Bodiga, S., et al. (2007) "Concurrent repletion of iron and zinc reduces intestinal oxidative damage in iron- and zinc-deficient rats", *World Journal of Gastroenterolog*, 13(43):5707-5717.
Bovell-Benjamin, A.C., et al. (2000) "Iron absorption from ferrous bisgycinate and ferric trisglycinate in whole maize is regulated by iron status", *American Journal of Clinical Nutrition*, 71:1563-1569.
Casanueva, E., et al. (2003) "Iron and oxidative stress in pregnancy", *J. Nutri.*, 133(5 Suppl. 2):1700S-1708S.
Chua, A.C.G., et al. (2010) "Iron: an emerging factor in colorectal carcinogenesis", *World Journal of Gastroenterology*, 16(6):663-672.
DSLD: Dietary Supplement Label Database of the U.S. National Library of Medicine, (http://www.dsld.nlm.nih.gov/dsld).
Gaboriau, F., et al. (2004) "Iron mobilization, cytoprotection, and inhibition of cell proliferation in normal and transformed rat hepatocyte cultures by the hydroxypyridinone CP411, compared to CP20: a biological and physicochemical study", *Biochemical Pharmacology*, 67(8):1479-1487.
Hutcheson, R., et al. (2003) "Hypotheses for the physiological pro-oxidant and antioxidant nature of Ca and Zn", ACS Northwest Regional Meeting 58, abstract 131.
INACG: International Nutritional Anemia Consultative Group (1998) "Guidelines for the use of iron supplements to prevent and treat iron deficiency anemia", (http://www.who.int/nutrition/publications/micronutrients/guidelines_for_Iron_supplementation.pdf).
Kilari, S., et al. (2010) "Zinc inhibits oxidative stress-reduced iron signaling and apoptosis in Caco-2 cells", *Free Radical Biology & Medicine*, 48:961-968.

(Continued)

*Primary Examiner* — Savitha M Rao
*Assistant Examiner* — Andrew P Lee

(57) ABSTRACT

An orally deliverable dosage system comprises (a) iron in a form of one or more physiologically acceptable iron grades, compounds and/or complexes; and (b) an agent to mitigate one or more gastrointestinal adverse effects of unabsorbed iron, said agent comprising one or both of a zinc component and a chelator component, said zinc component if present comprising one or more physiologically acceptable zinc compounds and/or complexes, and said chelator component if present comprising an ion-chelating compound formulated for release distal to the primary site of iron absorption in the duodenum.

11 Claims, No Drawings

(56) References Cited

OTHER PUBLICATIONS

Lin, A.M.Y. (2001) "Coexistence of zinc and iron augmented oxidative injuries in th enigrostriatal dopaminergic system of SD rats", *Free Radical Biology & Medicine*, 30(3):225-231.
Obolensky, A., et al. (2011) "Zinc-desferrioxamine attenuates retinal degeneration in the rd10 mouse model of retinitis pigmentosa", *Free Radical Biology & Medicine*, 51(8):1482-1491.
Pineda, O., et al. (1994) "Effectiveness of iron amino acid chelate on the treatment of iron deficiency anemia in adolescents", *Journal of Applied Nutrition*, 46(1&2):2-13.
Pineda, O., et al. (2001) "Effectiveness of treatment of iron-deficiency anemia in infants and young children with ferrous bis-glycinate chelate", *Nutrition*, 17:381-384.
Seril, D.N., et al. (2005) "Systemic iron supplementation replenishes iron stores without enhancing colon carcinogenesis in murine models of ulcerative colitis: comparison with iron-enriched diet", Dig. Dis. Sci., 50(4):696-707.
Sreedhar, B., et al. (2004) "A protective role for zinc on intestinal peroxidative damage during oral iron repletion", *Biochemical and Biophysical Research Communications*, 318:992-997.
Srigiridhar, K., et al. (1998) "Iron-deficient intestine is more susceptible to peroxidative damage during iron supplementation in rats", *Free Radical Biol. Med.*, 25(6):660-665.
European Search Report dated Apr. 3, 2017 from related EP Patent Application No. 14807576; 18 pgs.
Gomez et al., "Prevention of gastrointestinal iron absorption by chelation from an orally administered premixed deferaxamine/charcoal slurry," Annals of Emergency Medicine, 1997, vol. 30, No. 5, pp. 587-592.
Lynch et al., "Interaction of vitamin C and iron," Annals of the New York Academy of Sciences, 1980, vol. 355, pp. 32-44.
Sreedhar, "Concurent repletion of iron and zinc reduces intestincal oxidative damage in iron- and zinc-deficient rats," World Journal of Gastroenterolog, 2007, vol. 13, No. 43, pp. 5707-5717.
Sreedhar et al., "A protective role for zinc on intestinal peroxidative damage during oral iron repletion," Biochemical and Biophysical Research Communications, 2004, vol. 318, No. 4, pp. 992-997.
Ferrex(TM) 150 Forte Plus and Ferrex(TM) 150 Plus Capsules, Jan. 1, 2011, 2 pages.
Ferro sanol duodenal, Jan. 1, 2004, 2 pages.
Citric Acid, Jan. 1, 2007, 2 pages.
Examination Report dated Sep. 23, 2018 from related MX Patent Application No. MX/a/2015/016660; 2 pages.
Australian Search Report dated Jun. 7, 2016 from related AU Patent Application No. 2014275307; 3 pages.
Australian Search Report dated Feb. 13, 2017 from related AU Patent Application No. 2014275307; 3 pages.
Australian Notice of Acceptance dated Jun. 2, 2017 from related AU Patent Application No. 2014275307; 3 pages.
Examination Report dated Apr. 29, 2018 from related MX Patent Application No. MX/a/2015/016660; 3 pages.
Examination Report dated Apr. 29, 2018 from related IL Patent Application No. 242693; 9 pages.
Examination Report dated Jul. 9, 2019 from related EP Patent Application No. 14807576; 9 pages.
Examination Report dated Jan. 10, 2020 from related EP Patent Application No. 14807576; 11 pages.
Examination Report dated Nov. 29, 2019 from related MX Patent Application No. MX/a/2015/016660; 4 pages.
Examination Report dated Jan. 14, 2020 from related BR Patent Application No. BR112015029468-5; 5 pages.
Examination Report dated Jan. 23, 2020 from related IL Patent Application No. 242693, 6 pages.
Examination Report dated Jan. 26, 2021 from related CA Patent Application No. 2913413, 3 pages.
Examination Report dated Jul. 31, 2020 from related EP Patent Application No. 1407576; 5 pages.
Decision to Grant dated Jul. 1, 2021 from related EP Patent Application No. 1407576; 2 pages.
Robinson, J.R., and Gauger, L.J., "Formulation of controlled-release products" Journal of Allergy and Clinical Immunology, 1986, 78(4.2): 676-681.
Examination Report dated Oct. 28, 2021 from related BR Patent Application No. 112015029468-5; 4 pages.

\* cited by examiner

IRON SUPPLEMENT

CROSS-REFERENCE TO RELATED APPLICATIONS

This patent application claims the benefit of U.S. provisional application 61/831,879 filed on 6 Jun. 2013, the contents of which are hereby incorporated by reference in their entirety.

FIELD

The present invention relates to dosage systems useful in providing supplementary iron to a human subject in need thereof, more particularly to a human subject having high iron demand, as for example in pregnancy, or an iron deficiency condition such as iron deficiency anemia; or a human subject at elevated risk of such a condition. The invention further relates to methods of nutritional supplementation to such a subject comprising orally administering a dosage system of the invention. The invention still further relates to compositions and methods for mitigating gastrointestinal adverse effects of unabsorbed iron.

BACKGROUND

Iron is an essential nutrient for animal, including human, life, because of its critical role in cellular energy pathways, not least as a component of cytochromes in the mitochondria of all living cells and, more specifically, of hemoglobin in red blood cells. It has two stable oxidation states, $Fe^{++}$ and $Fe^{+++}$. Through exchange of electrons with donor or acceptor molecules, interconversion of these oxidation states of iron is a fundamental process at the heart of the body's energy economy.

The essential role of iron in human nutrition is well known. It is less widely appreciated, however, that the selfsame facility of iron for oxidative electron transfer can lead to toxicity wherever the iron is "free", i.e., not safely "packaged" within carrier proteins such as transferrin or storage proteins such as ferritin. Such "free" iron can catalyze conversion of superoxide to the even more reactive hydroxyl radical, and may thus be implicated not only in acute toxicity but, through damage to DNA, in carcinogenesis.

Absorption of iron from the gastrointestinal tract into the bloodstream occurs principally in the duodenum. The lower intestinal tract, i.e., those parts distal to the duodenum, including jejunum, ileum and colon, are exposed to excess iron that escapes duodenal uptake, and can transport the iron locally into cells bordering the intestinal lumen. This iron becomes "trapped" in the luminal enterocytes, which have no mechanism for re-releasing it and only very limited capacity for transfer to the circulatory system. Such trapped iron in the lower intestinal tract can cause oxidative toxicity and can be a risk factor for colorectal cancer (Seril (2005) *Dig. Dis. Sci.* 50, 696-707; Chua et al. (2010) *World J. Gastroenterol.* 16, 663-672).

The harmful colonic trapping of iron appears to be increased in iron deficiency conditions (Srigirdhar & Nair (1998) *Free Radical Biol. Med.* 25, 660-665)—the very conditions in which elevated doses of supplemental iron may be indicated.

At typical daily doses of iron supplied by over-the-counter nutritional supplements, namely about 15 to 30 mg, the risk of gastrointestinal adverse effects due to unabsorbed iron is relatively low. However, as daily dose increases beyond about 30 mg, a progressively greater portion of that dose escapes duodenal absorption (Casanueva & Viteri (2003) *J. Nutr.* 133, 1700S-1708S) and becomes available to cause adverse effects in the lower intestinal tract, most particularly in the colon. Recommended doses of iron for treatment of iron deficiency anemia, for example in pregnancy, range from 60 to 120 mg per day (International Nutritional Anemia Consultative Group; http://www.who.int/nutrition/publications/micronutrients/guidelines_for_iron_supplementation.pdf).

U.S. Pat. Nos. 5,516,925 and 8,007,846 describe iron amino acid chelates including ferrous asparto glycinate suitable for use in nutritional supplements.

Some nutritional supplements delivering up to 30 mg iron additionally supply zinc, for example in amounts up to 32 mg. See, for example, *Dietary Supplements Labels Database* of the U.S. National Library of Medicine (http://dietarysupplements.nlm.nih.gov).

Zinc is a competitive inhibitor of iron uptake (Bodiga & Krishnapillai (2007) *World J. Gastroenterol.* 13, 5707-5717); however, it is not known to what extent, if at all, this results in an increase in unabsorbed iron at supplemental iron doses greater than 30 mg per day, for example at the high doses of 60 to 120 mg per day recommended in iron deficiency anemia. It has been reported that zinc can play a protective role in reducing iron-mediated intestinal oxidative damage (Sreedhar et al. (2004) *Biochem. Biophys. Res. Comm.* 318, 992-997; Bodiga & Krishnapillai (2007) supra).

Animal feeds containing added iron and zinc are known; see for example Chinese patent publication no. CN 102318764 A. A mineral premix containing, per kg, 100-250 g ferrous glycinate and 100-200 g zinc glycinate is mentioned in Chinese patent publication no. CN 101744120 B.

Chinese patent publication no. CN 1965697 A appears to relate to a drinking product containing auxiliary materials selected from, inter alia, EDTA, ferrous glycinate, zinc gluconate and zinc glycinate.

Notwithstanding the above-referenced Chinese publication, use of chelators such as EDTA that are poorly or not at all absorbed following oral administration is generally antagonistic to iron nutrition, as these chelators can bind free iron, rendering it unavailable for uptake. In cases of iron toxicity, poorly absorbed chelating agents such as EDTA or DFO (also known as deferoxamine or desferrioxamine) are administered parenterally. However, studies have been conducted, with mixed results, to test feasibility of reducing iron overload by oral administration of such chelating agents (see review by Algren (undated), http://www.who.int/selection_medicines/committees/expert/18/applications/iron/en/index.html).

In U.S. Pat. No. 5,075,469 it is proposed that iron can displace zinc from a zinc-DFO complex. Example 10 thereof relates to a sterile solution for oral administration containing 500 mg Desferal™ (DFO) and 10.4 mg zinc chloride.

Hutcheson (2003) *ACS Northwest Regional Meeting* 58, abstract 131 proposes that zinc can displace iron in both ferrous and ferric oxidation states from EDTA.

Documents cited above are incorporated herein by reference in their entirety.

Nutritional supplement manufacturers and official dietary recommendations have so far inadequately addressed the risk of gastrointestinal adverse effects of iron supplementation, especially at daily doses of about 0.6 mmol (33.5 mg) and higher. This deficiency in the art is corrected by the invention described below.

SUMMARY

According to one aspect of the present invention, there is provided an orally deliverable nonfood dosage system comprising
(a) iron in a form of one or more physiologically acceptable iron grades, compounds and/or complexes, in a total elemental iron amount of about 0.6 to about 3 mmol; and
(b) an agent to mitigate one or more gastrointestinal adverse effects of unabsorbed iron, this agent comprising one or both of a zinc component and a chelator component, such zinc component if present comprising one or more physiologically acceptable zinc compounds and/or complexes, in a total elemental zinc amount of about 0.1 to about 1.2 mmol per mmol iron, and such chelator component if present comprising an ion-chelating compound formulated for release distal to the primary site of iron absorption in the duodenum;
in a form of a single composition containing said iron and said agent, or in a form of an iron-containing composition and a companion composition containing at least one component of said agent.

In a related embodiment there is provided an orally deliverable dosage system comprising
(a) iron in a form of one or more physiologically acceptable iron grades, compounds and/or complexes including ferrous asparto glycinate, in a total elemental iron amount of about 0.06 to about 3 mmol; and
(b) an agent to mitigate one or more gastrointestinal adverse effects of unabsorbed iron, this agent comprising one or both of a zinc component and a chelator component, such zinc component if present comprising one or more physiologically acceptable zinc compounds and/or complexes, in a total elemental zinc amount of about 0.1 to about 1.2 mmol per mmol iron, and such chelator component if present comprising an ion-chelating compound formulated for release distal to the primary site of iron absorption in the duodenum;
in a form of a single composition containing said iron and said agent, or in a form of an iron-containing composition and a companion composition containing at least one component of said agent.

In a further related embodiment there is provided an orally deliverable dosage system comprising
(a) iron in a form of one or more physiologically acceptable iron grades, compounds and/or complexes, in a total elemental iron amount of about 0.06 to about 3 mmol; and
(b) an agent to mitigate one or more gastrointestinal adverse effects of unabsorbed iron, this agent being formulated for release distal to the primary site of iron absorption in the duodenum and comprising one or both of a zinc component and a chelator component, such zinc component if present comprising one or more physiologically acceptable zinc compounds and/or complexes, and such chelator component if present comprising one or more ion-chelating compounds;
in a form of a single composition containing said iron and said agent, or in a form of an iron-containing composition and a companion composition containing said agent.

The present invention also provides methods for supplementing iron nutrition in a human subject in need thereof, comprising orally administering the dosage system of any of the embodiments described above.

The present invention further provides a method for mitigating one or more gastrointestinal adverse effects of unabsorbed iron in a human subject receiving supplemental iron in a total elemental iron amount of about 0.6 to about 3 mmol, the method comprising orally administering to the subject one or more physiologically acceptable zinc compounds and/or complexes, in a total elemental zinc amount of about 0.1 to about 1.2:1 mmol per mmol iron.

In a still further embodiment there is provided an orally deliverable companion composition comprising an agent for mitigating one or more gastrointestinal adverse effects of unabsorbed iron, this agent being formulated for release distal to the primary site of iron absorption in the duodenum and comprising one or both of a zinc component and a chelator component, such zinc component if present comprising one or more physiologically acceptable zinc compounds and/or complexes, and such chelator component if present comprising one or more ion-chelating compounds; said composition being substantially free of any other pharmaceutical active ingredient.

There is also provided a method for mitigating one or more gastrointestinal adverse effects of unabsorbed iron in a human subject receiving supplemental iron in a total elemental iron amount of about 0.06 to about 3 mmol, the method comprising orally administering to the subject a companion composition as described immediately above.

Other embodiments, variants thereof and modes of practicing the invention will be evident from the more detailed description that follows.

DETAILED DESCRIPTION

The word "about", when qualifying any amount herein, will be understood to mean±10%, preferably ±5%, of the amount so qualified, unless otherwise indicated.

Dosage System

A "dosage system" in the present context means a single composition or small plurality of compositions (e.g., a first and a second composition) containing a specified dose, typically a daily dose, of iron, together with an agent or agents to mitigate one or more gastrointestinal adverse effects of unabsorbed iron. A dosage system of the invention is orally deliverable, i.e., can be administered per os, and can be referred to as an oral dosage system. Thus, a dosage system as provided herein is formulated for oral dosing in an animal, most particularly a human, subject.

The dosage system provided herein takes the form of one to a small plurality of dosage forms such as tablets, capsules, granules, lozenges, solutions or suspensions, formulated using conventional pharmaceutical excipients and adapted for oral administration. The dosage system provided herein can also be referred to as an oral supplement.

Dosage systems are described herein with particular reference to single compositions comprising both the iron component and the mitigating agent component. If convenient or desired, however, the iron component can be delivered via a first composition and the mitigating agent or agents via a second (or "companion") composition. In such a case, the first and second compositions can take the same, similar or different forms, for example, two tablets; or a tablet and a capsule; or a capsule and a solution, etc.

According to some embodiments, the dosage system is described herein as a "nonfood dosage system". In other words, such a dosage system is self-contained and is not a component of, nor an additive for admixture with, food, feed or beverage, though it can, if convenient or desired, be administered concurrently with food, feed or beverage, for example at a mealtime. Conventional pharmaceutical excipients present in the dosage system, for example dextrose, starch, etc., that contribute in a minor way to the subject's caloric intake are not considered "food" for present purposes, thus a dosage system comprising such excipients can still be a "nonfood dosage system" as provided herein.

According to other embodiments, the dosage system is not limited to a nonfood dosage system. Where "nonfood" is not specified, it will be understood that the dosage system can take the form of a food, feed, beverage or food additive, or can be a nonfood dosage system as defined above. Nonfood dosage systems are generally preferred herein as providing a more precisely metered dose of iron and mitigating agent.

The amount of any ingredient contained in a dosage system as described herein will be understood to be the amount in a single discrete dosage form such as a tablet, capsule or lozenge. Typically such a discrete dosage form provides a full daily dose, but where a high dose is indicated, more than one such discrete dosage form can be administered per day. For example, for a human subject requiring 100 mg iron per day, two tablets or capsules each containing 50 mg iron can be administered. Where the dosage system is in a non-discrete form such as granules or a solution or suspension, the amount of any ingredient contained therein will be understood to be the amount in a specific volume, e.g., 5 ml or 10 ml, providing a single daily dose.

Unless otherwise specified herein, the term "controlled release" or "delayed release" refers specifically to release of an ingredient from an orally administered composition or dosage system in one or more zones of the intestinal tract distal to the duodenum, for example in the jejunum, ileum and/or colon, without substantial release in the duodenum or proximal thereto.

Iron Component

Where a dosage system does not comprise a controlled release component as described herein, iron is present, in a form of one or more physiologically acceptable iron grades, compounds and/or complexes, in a total elemental iron amount of about 0.6 mmol (33.5 mg) to about 3 mmol (168 mg), except where the iron is partly or wholly in the form of ferrous asparto glycinate, in which case a total elemental iron amount of about 0.06 mmol (3.35 mg) to about 3 mmol (168 mg), for example about 0.3 mmol (16.8 mg) to about 3 mmol (168 mg), is present in the dosage system. Where a dosage system comprises a controlled release component as described herein, iron is present (though not in controlled release form) in a total elemental iron amount of about 0.06 to about 3 mmol, for example about 0.3 to about 3 mmol, again in a form of one or more physiologically acceptable iron grades, compounds and/or complexes. In all cases, however, a particularly useful dosage system of the invention is a nonfood dosage system comprising iron in a total elemental iron amount of about 0.6 to about 3 mmol. In certain embodiments, the total elemental iron content of the dosage system is at least about 20 mg (0.36 mmol), at least about 30 mg (0.54 mmol), at least about 40 mg (0.72 mmol), at least about 50 mg (0.90 mmol) or at least about 60 mg (1.07 mmol). In certain embodiments, the total elemental iron content of the dosage system is no greater than about 150 mg (2.69 mmol), no greater than about 135 mg (2.42 mmol) or no greater than about 120 mg (2.15 mmol).

Physiologically acceptable grades of elemental iron that can be used in a dosage system of the invention include without limitation carbonyl iron and electrolytic iron. Physiologically acceptable iron compounds and complexes that can be used in a dosage system of the invention include without limitation iron oxides, for example iron(II) oxide (ferrous oxide), ferrous sulfate, ferrous ascorbate, iron amino acid chelates (e.g., ferrous aspartate, ferrous asparto glycinate, ferrous bisglycinate and ferrous histidinate), ferrous citrate, ferrous fumarate, ferrous gluconate, ferrous ketoglutarate, ferrous malate, ferrous succinate, iron-polysaccharide complex and heme-iron polypeptide. Compounds and complexes in the iron(II) or ferrous ($Fe^{++}$) oxidation state are generally preferred but in some instances, compounds and complexes in the iron (III) or ferric ($Fe^{+++}$) form could be preferred. Examples of ferric forms of iron that may be used include, iron (III) oxide (ferric oxide), ferric oxide-hydroxide, ferric acetate, ferric bromide, ferric chloride, ferric chromate, ferric citrate, ferric ammonium citrate, ferric fluoride, ferric hydroxide, ferric nitrate, ferric polymaltose, ferric phosphate, ferric pyrophosphate, ferric oxalate, ferric ammonium oxalate, ferric sulfate, ferroglycine sulfate, ferric sulfide, ferric glycinate (Iron Taste-Free® of Albion Laboratories, Inc. or a product technically equivalent thereto) and EDTA ferric sodium salt.

In a particular embodiment, iron is present in the form of ferrous asparto glycinate, for example as the product Sumalate® of Albion Laboratories, Inc. or a product technically equivalent thereto. In another particular embodiment, iron is present in the form of ferrous bisglycinate, for example as the product Ferrochel® of Albion Laboratories, Inc. or a product technically equivalent thereto. In yet another embodiment, iron is present in the form of ferric glycinate, for example as the product Iron Taste-Free® of Albion Laboratories, Inc. or a product technically equivalent thereto.

Mixtures of two or more of the above iron grades, compounds and complexes can be used if desired. In a particular embodiment, any of the dosage systems provided herein may have both ferrous asparto glycinate (Sumalate®) and ferrous bisglycinate (Ferrochel®) present in a total elemental iron amount of about 0.06 mmol (3.35 mg) to about 3 mmol (168 mg), for example about 0.3 mmol (16.8 mg) to about 3 mmol (168 mg). In another particular embodiment, any of the dosage systems provided herein may have ferric glycinate (Iron Taste-Free®) combined with either ferrous asparto glycinate (Sumalate®) or ferrous bisglycinate (Ferrochel®) or both present in a total elemental iron amount of about 0.06 mmol (3.35 mg) to about 3 mmol (168 mg), for example about 0.3 mmol (16.8 mg) to about 3 mmol (168 mg).

Zinc Component

In those dosage systems of the invention that do not comprise a controlled release component as described herein, zinc is present in a total elemental zinc amount of about 0.1 to about 1.2 mmol per mmol iron. A zinc:iron molar ratio lower than about 0.1:1 is unlikely to afford significant benefit over no zinc at all; at a molar ratio greater than about 1.2:1, the benefits of zinc contemplated herein, particularly the mitigation of intestinal adverse effects of unabsorbed iron, may be outweighed by the tendency of zinc to inhibit iron absorption in the duodenum. In various embodiments, the zinc:iron molar ratio is at least about 0.2:1, at least about 0.4:1 or at least about 0.6:1, or at least 0.8:1. A zinc:iron molar ratio no greater than about 1:1 is preferred according to some embodiments.

In yet further embodiments, the amount of zinc to amount of iron present in the dosage systems can be from about 0.1 to about 0.5 mg zinc per 1 mg iron, particularly from about 0.3 to about 0.8 mg zinc per 1 mg iron, more particularly from about 0.6 mg to about 1 mg zinc per 1 mg iron, and even more particularly from about 0.9 to about 1.42 mg zinc per 1 mg iron.

In those dosage systems of the invention that comprise a controlled-release zinc component, the amount of such zinc is not narrowly critical as it is not available to interfere with iron absorption in the duodenum. Illustratively, controlled-release zinc can be present in the dosage system in a total elemental zinc amount of about 0.05 to about 3 mmol. In certain embodiments, particularly where iron is present in a total elemental iron amount of at least about 0.6 mmol, the total elemental zinc content of the dosage system, whether in controlled release form or otherwise, is at least about 10 mg (0.15 mmol), at least about 20 mg (0.31 mmol), at least about 30 mg (0.46 mmol) or at least about 40 mg (0.61 mmol). In certain embodiments, the total elemental zinc content of the dosage system, whether in controlled release form or otherwise, is no greater than about 160 mg (2.45 mmol), no greater than about 120 mg (1.83 mmol) or no greater than about 80 mg (1.22 mmol).

Physiologically acceptable zinc compounds and complexes that can be used in a dosage system of the invention include without limitation zinc oxide, zinc sulfate, zinc amino acid chelates (e.g., zinc arginate, zinc aspartate, zinc bisglycinate, citrated zinc bisglycinate and zinc histidinate), zinc acetate, zinc acetate dihydrate, zinc ascorbate, zinc citrate, zinc gluconate, zinc ketoglutarate, zinc malate, zinc picolinate, zinc stearate and zinc succinate. Mixtures of two or more of the above zinc compounds and complexes can be used if desired. In a particular embodiment, Zinc Bisglycinate Chelate Taste Free™ zinc bisglycinate chelate and/or zinc arginate chelate are present in any of the dosage systems provided herein to provide a total amount of elemental zinc discussed above (for either a controlled release formulation or a non-controlled release formulation).

As noted above, the zinc component if present can be formulated together with or separately from the iron component. Where the zinc component is provided in controlled release form, any suitable controlled release mechanism can be employed, for example time-release or pH-triggered release, as provided for example by enteric coatings well known to those of skill in the art.

In a particular embodiment, the dosage system comprises (in addition to the iron component) a zinc component but no controlled release component as described herein. In this embodiment the dosage system is a nonfood dosage system with a total elemental iron content of about 0.6 to about 3 mmol and a total elemental zinc content of about 0.1 to about 1.2 mmol per mmol iron.

Chelator Component

The chelator component, in those dosage systems of the invention that comprise one, is to be distinguished from chelated forms of iron and zinc as mentioned above. It comprises one or more ion-chelating compounds formulated for delayed or controlled release, more particularly for release distal to the primary site of iron absorption in the duodenum. Typically the ion-chelating compound(s) selected are poorly absorbed from the gastrointestinal tract, their function being to scavenge unabsorbed iron for safe elimination in fecal waste, thereby reducing exposure of the mucosa and enterocytes of the lower gastrointestinal tract to free iron. Any suitable controlled release mechanism can be employed, for example time-release or pH-triggered release, as provided for example by enteric coatings well known to those of skill in the art.

Suitable ion-chelating compounds include without limitation ethylene diamine tetraacetic acid (EDTA), deferoxamine (DFO), deferiprone and deferasirox. Ion-chelating compounds that form hexadentate ligands, of which EDTA and DFO are examples, are generally preferred, as these form complexes with iron at a 1:1 molar ratio. (Bidentate ion-chelating compounds form complexes at a 3:1 molar ratio with iron, and consequently must be present in significantly higher amounts for equivalent efficacy in iron chelation.) Mixtures of two or more ion-chelating compounds can be used if desired. Preferably the chelating compound is used in the form of an apochelator, i.e., uncomplexed with any metal ion. If the chelating compound is already complexed, it should be with a metal that is readily replaced by iron.

A dosage system of the invention having a chelator component typically comprises such ion-chelating compound(s) in a total amount of about 30 to about 1000 mg, particularly from about 60 to about 1000 mg, and more particularly from about 100 to about 1000 mg. In certain embodiments, the dosage system comprises at least about 200 mg or at least about 300 mg of such ion-chelating compound(s). In certain embodiments, the dosage system comprises no more than about 900 mg or no more than about 800 mg of such ion-chelating compound(s).

As noted above, the chelator component if present can be formulated together with or separately from the iron component. In a particular embodiment, the dosage system comprises (in addition to the iron component) both a zinc component and a chelator component, each as described above.

Other Ingredients

A dosage system of the invention can optionally contain additional ingredients. For example, additional mineral nutrients such as calcium, magnesium, chromium, copper, manganese, molybdenum and vanadium in the form of salts and/or complexes of these elements can be present, as can vitamins such as ascorbic acid, salts and esters thereof, and vitamin D.

Illustrative salts and complexes of minerals other than iron and zinc that can optionally be present include calcium carbonate, monocalcium phosphate, dicalcium phosphate, hydroxyapatite (including microcrystalline hydroxyapatite), calcium citrate tetrahydrate, calcium citrate malate, calcium formate, calcium gluconate, calcium glycerophosphate, calcium bisglycinate, calcium lactate, calcium levulinate, dicalcium malate (for example DimaCal® of Albion Laboratories, Inc. and products technically equivalent thereto), calcium succinate, calcium tartrate, magnesium aspartate, magnesium creatine chelate, magnesium glycinate, magnesium glycyl glutamine chelate, magnesium lysyl glycinate, dimagnesium malate, chromium nicotinate glycinate, copper glycinate, manganese glycinate, molybdenum glycinate, vanadium nicotinate glycinate and combinations thereof.

The term "vitamin D" herein includes not only cholecalciferol (vitamin $D_3$) but analogs, precursors, provitamins and metabolites thereof having vitamin D activity including without limitation ergocalciferol (vitamin $D_2$), 25-hydroxyergocalciferol, 25-hydroxycholecalciferol (25-OH vitamin D) and 1,25-dihydroxycholecalciferol (1,25-diOH vitamin D).

The dosage system optionally further comprises one or more excipients, selected for example from those conventionally used in preparing pharmaceutical formulations such as diluents, binding agents, dispersants, wetting agents, lubricants, glidants, etc. Many excipients have two or more functions in a pharmaceutical composition. Characterization herein of a particular excipient as having a certain function, e.g., diluent, binding agent, disintegrant, etc., should not be read as limiting to that function.

Suitable diluents illustratively include, either individually or in combination, lactose, including anhydrous lactose and lactose monohydrate; lactitol; maltitol; mannitol; sorbitol; xylitol; dextrose and dextrose monohydrate; fructose; sucrose and sucrose-based diluents such as compressible sugar, confectioner's sugar and sugar spheres; maltose; inositol; hydrolyzed cereal solids; starches (e.g., corn starch, wheat starch, rice starch, potato starch, tapioca starch, etc.), starch components such as amylose and dextrates, and modified or processed starches such as pregelatinized starch; dextrins; celluloses including powdered cellulose, microcrystalline cellulose, silicified microcrystalline cellulose, food grade sources of α- and amorphous cellulose and powdered cellulose, and cellulose acetate; magnesium carbonate; magnesium oxide; bentonite; kaolin; sodium chloride; and the like.

Binding agents or adhesives are useful excipients, particularly where the composition is in the form of a tablet. Such binding agents and adhesives should impart sufficient cohesion to the blend being tableted to allow for normal processing operations such as sizing, lubrication, compression and packaging, but still allow the tablet to disintegrate upon ingestion. Suitable binding agents and adhesives include, either individually or in combination, acacia; tragacanth; glucose; polydextrose; starch including pregelatinized starch; gelatin; modified celluloses including methylcellulose, carmellose sodium, hydroxypropylmethylcellulose (HPMC or hypromellose), hydroxypropylcellulose, hydroxyethylcellulose and ethylcellulose; dextrins including maltodextrin; zein; alginic acid and salts of alginic acid, for example sodium alginate; magnesium aluminum silicate; bentonite; polyethylene glycol (PEG); polyethylene oxide; guar gum; polysaccharide acids; polyvinylpyrrolidone (povidone), for example povidone K-15, K-30 and K-29/32; polyacrylic acids (carbomers); polymethacrylates; and the like.

Suitable disintegrants include, either individually or in combination, starches including pregelatinized starch and sodium starch glycolate; clays; magnesium aluminum silicate; cellulose-based disintegrants such as powdered cellulose, microcrystalline cellulose, methylcellulose, low-substituted hydroxypropylcellulose, carmellose, carmellose calcium, carmellose sodium and croscarmellose sodium; alginates; povidone; crospovidone; polacrilin potassium; gums such as agar, guar, locust bean, karaya, pectin and tragacanth gums; colloidal silicon dioxide; and the like.

Suitable wetting agents include, either individually or in combination, quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10 and octoxynol 9; poloxamers (polyoxyethylene and polyoxypropylene block copolymers); polyoxyethylene fatty acid glycerides and oils, for example polyoxyethylene (8) caprylic/capric mono- and diglycerides, polyoxyethylene (35) castor oil and polyoxyethylene (40) hydrogenated castor oil; polyoxyethylene alkyl ethers, for example ceteth-10, laureth-4, laureth-23, oleth-2, oleth-10, oleth-20, steareth-2, steareth-10, steareth-20, steareth-100 and polyoxyethylene (20) cetostearyl ether; polyoxyethylene fatty acid esters, for example polyoxyethylene (20) stearate, polyoxyethylene (40) stearate and polyoxyethylene (100) stearate; sorbitan esters; polyoxyethylene sorbitan esters, for example polysorbate 20 and polysorbate 80; propylene glycol fatty acid esters, for example propylene glycol laurate; sodium lauryl sulfate; fatty acids and salts thereof, for example oleic acid, sodium oleate and triethanolamine oleate; glyceryl fatty acid esters, for example glyceryl monooleate, glyceryl monostearate and glyceryl palmitostearate; sorbitan esters, for example sorbitan monolaurate, sorbitan monooleate, sorbitan monopalmitate and sorbitan monostearate; tyloxapol; and the like.

Lubricants reduce friction between a tableting mixture and tableting equipment during compression of tablet formulations. Suitable lubricants include, either individually or in combination, glyceryl behenate; stearic acid and salts thereof, including magnesium, calcium and sodium stearates; hydrogenated vegetable oils; glyceryl palmitostearate; talc; waxes; sodium benzoate; sodium acetate; sodium fumarate; sodium stearyl fumarate; PEGs (e.g., PEG 4000 and PEG 6000); poloxamers; polyvinyl alcohol; sodium oleate; sodium lauryl sulfate; magnesium lauryl sulfate; and the like.

Glidants improve flow properties and reduce static in a tableting mixture. Suitable glidants include, either individually or in combination, colloidal silicon dioxide, starch, powdered cellulose, sodium lauryl sulfate, magnesium trisilicate and metallic stearates.

Other excipients such as buffering agents, stabilizers, antioxidants, antimicrobials, colorants, flavors and sweeteners are known in the pharmaceutical art and can be used. Tablets can be uncoated or can comprise a core that is coated, for example with a nonfunctional film or a release-modifying or enteric coating. Capsules can have hard or soft shells comprising, for example, gelatin and/or HPMC, optionally together with one or more plasticizers.

A dosage system of the invention can be prepared by any of the conventional processes of pharmacy well known to those of skill in the art.

Companion Composition

In another embodiment of the invention an orally deliverable composition comprises an agent for mitigating one or more gastrointestinal adverse effects of unabsorbed iron, this agent being formulated for release distal to the primary site of iron absorption in the duodenum. The mitigating agent comprises one or both of a zinc component and a chelator component, such zinc component if present comprising one or more physiologically acceptable zinc compounds and/or complexes, and such chelator component if present comprising one or more ion-chelating compounds. The composition is substantially free of any other pharmaceutical active ingredient. Any suitable controlled release mechanism can be employed, for example time-release or pH-triggered release, as provided for example by enteric coatings well known to those of skill in the art. Optionally zinc can be present additionally in immediate release form. Such a composition is useful as a companion composition for administration along with an iron supplement.

A companion composition as provided herein comprises one or more dosage units. In a particular embodiment, the companion composition comprises one or more physiologically acceptable zinc compounds and/or complexes, whether in controlled release form or otherwise, in a total elemental zinc amount of about 0.05 to about 3 mmol per dosage unit. In certain embodiments, the total elemental zinc content of such a companion composition is at least about 10 mg (0.15 mmol), at least about 20 mg (0.31 mmol), at least about 30 mg (0.46 mmol) or at least about 40 mg (0.61 mmol) per dosage unit. In certain embodiments, the total elemental zinc content of such a companion composition is no greater than about 160 mg (2.45 mmol), no greater than about 120 mg (1.83 mmol) or no greater than about 80 mg (1.22 mmol) per dosage unit.

Physiologically acceptable zinc compounds and complexes that can be used in such a companion composition include without limitation zinc oxide, zinc sulfate, zinc amino acid chelates (e.g., zinc arginate, zinc aspartate, zinc bisglycinate, citrated zinc bisglycinate and zinc histidinate), zinc acetate, zinc acetate dihydrate, zinc ascorbate, zinc citrate, zinc gluconate, zinc ketoglutarate, zinc malate, zinc picolinate, zinc stearate and zinc succinate. Mixtures of two or more of the above zinc compounds and complexes can be used if desired. In a particular embodiment, Zinc Bisglycinate Chelate Taste Free™ zinc bisglycinate chelate and/or zinc arginate chelate are present in any of the companion compositions provided herein to provide a total amount of elemental zinc discussed above (for either a controlled release formulation or a non-controlled release formulation).

In another particular embodiment, the companion composition comprises in controlled release form one or more ion-chelating compounds, preferably such compounds exhibiting poor oral bioavailability. Suitable ion-chelating compounds include without limitation those mentioned above, including EDTA, DFO, deferiprone and deferasirox. Mixtures of two or more ion-chelating compounds can be used if desired. Preferably the chelating compound is hexadentate and is used in the form of an apochelator, i.e., uncomplexed with any metal ion. If the chelating compound is already complexed, it should be with a metal that is readily replaced by iron.

A companion composition of the present embodiment typically comprises such ion-chelating compound(s) in a total amount of about 100 to about 1000 mg per dosage unit. In certain embodiments, each dosage unit (e.g., tablet, capsule, lozenge, granules, solution or suspension), formulated using conventional excipients and adapted for oral administration, comprises at least about 200 mg or at least about 300 mg of such ion-chelating compound(s). In certain embodiments, each dosage unit comprises no more than about 900 mg or no more than about 800 mg of such ion-chelating compound(s).

The companion composition optionally further comprises one or more excipients, selected for example from those conventionally used in preparing pharmaceutical formulations such as diluents, binding agents, dispersants, wetting agents, lubricants, glidants, etc., as more fully exemplified above.

Method for Supplementing Iron Nutrition

Also provided by the present invention is a method for supplementing iron nutrition in a human subject in need thereof, comprising orally administering a dosage system as described above to the subject. In most cases one such dosage system per day will suffice, but in particular situations it may be necessary to increase the dose, in which case more than one, but rarely more than two, such dosage systems can be administered per day.

The above method can be used to treat various conditions of iron deficiency, disease states or other medical conditions associated with iron deficiency, in a human subject having such a condition. It can also be used prophylactically in a human subject not yet experiencing symptoms of an iron deficiency condition or a medical condition associated therewith, but at risk of developing such a condition, for example during pregnancy.

Iron is involved in energy metabolism as an oxygen carrier in hemoglobin, and as a structural component of cytochromes in electron transport. Additionally, iron is a structural component at the catalytic site of a large number of enzymes covering a wide array of diverse metabolic functions. These include neurotransmitter synthesis and function, phagocyte antimicrobial activity, hepatic detoxification systems, and synthesis of DNA, collagen and bile acids. Iron deficiency limits oxygen delivery to cells, resulting in fatigue, poor work performance and decreased immunity. Thus, the present method can be used to supply iron for the purposes described herein and others well known in the art.

In one embodiment, a dosage system of the invention can be orally administered to a subject in need thereof as a hematinic, i.e., an agent to increase the level of hemoglobin in the subject's blood, for example in prophylaxis or therapy for conditions of iron deficiency anemia. In other embodiments, a dosage system of the invention can be orally administered to a subject in need thereof as prophylaxis or therapy for iron deficiencies and associated complications arising from any of the following: pathologic diseases that would result in hematologic consequences; chronic diseases such as chronic renal failure; HIV; connective tissue disease; immune-related and autoimmune diseases; cancer; rheumatoid arthritis; conditions leading to or contributing to blood loss such as gastrointestinal bleeding; gastrointestinal diseases; peptic ulcer disease; gastritis; colon cancer; colon polyps; inflammatory bowel disease; tropical sprue; celiac disease; infectious diseases; parasites including hookworm; malaria; iatrogenic complications arising from the administration of drugs such as erythropoetin, NSAIDs, steroids, agents causing reduced platelet function, proton pump inhibitors or H2 antagonists; post-surgical complications of procedures such as gastrectomy, gastric bypass, vagotomy, donating blood for blood banks or in preparation for elective surgery such as orthopedic surgery, joint replacement or gynecological surgery including for fibroid uterus.

In one embodiment the present method can be used in prophylaxis or therapy for a condition associated with the childbearing years, for example where gestational and neurodevelopmental effects on offspring are well recognized. The childbearing years in the present context include pre-natal, pregnancy, menses, lactation and post-pregnancy. Thus, a dosage system described herein can be a pre-natal vitamin, which can be administered to a subject/patient for example before, during or after pregnancy.

In one embodiment the present method can be used in prophylaxis or therapy for a neurological condition such as restless leg syndrome, cognitive complications, neurodevelopmental complications or chronic fatigue; or for optimization of exercise and peak physiologic performance.

In one embodiment the present method can be used to promote competitive absorption resulting in reduced absorption of toxic levels of heavy metals such as lead, mercury, arsenic or cadmium through consumption or inhalation from cigarette smoke.

Efficacy of the present method can be measured by conventional and relatively straightforward biochemical markers which are currently well recognized by those skilled in the art to demonstrate effective administration such as, for example, serum iron, serum ferritin, iron binding capacity, transferrin, and transferrin saturation. These classical measurements may be helpful to demonstrate an effective dose for many well recognized indications, for example, a rise in the hemoglobin, iron or ferritin levels in iron deficiency anemia, but may not adequately reflect more subtle iron deficiency states such as, but not limited to, restless leg syndrome, in which only a clinical response to administration of said compound may be measurable. Examples of such clinical responses include decreased observed muscle restlessness as well as decreased involuntary muscle activity measured by neuromuscular stimulatory tests, sleep studies and the like. A greater understanding of the complex metabolic processes involved in iron absorption and metabolism has led to newer biomedical markers that are and could be more useful to detect changes in iron absorption, transport and metabolism, and clinical implications thereof such as red cell and reticulocyte indices, plasma cytokines and iron metabolism regulators such as hepcidin, iron regulatory proteins, iron transport proteins such as transferrin receptor, ferroportin as well as divalent metal transporters (DMTs), duodenal cytochromes and hephaestin, to name only a few of the types of biomarkers that could be useful in biochemical assays. The ratio of serum transferrin receptor (sTFR) to serum ferritin (the R/F ratio) has been shown to be an excellent biochemical marker for iron storage levels. These and other biomarkers, such as markers of oxidative stress or cell damage, can also be used to determine whether toxic or other damaging effects from an abundance of iron in the body are likely to be present or occur.

Method for Mitigating Adverse Effects of Supplemental Iron

Also provided by the present invention is a method for mitigating one or more gastrointestinal adverse effects of unabsorbed iron in a human subject receiving supplemental iron in a total elemental iron amount of about 0.6 to about 3 mmol, for example about 40 to about 150 mg, about 50 to about 135 mg, or about 60 to about 120 mg. The method comprises orally administering one or both of a zinc component and a chelator component, the zinc component if present comprising one or more physiologically acceptable zinc compounds and/or complexes, in a total elemental zinc amount of about 0.1 to about 1.2:1 mmol per mmol supplemental iron, and the chelator component if present comprising one or more ion-chelating compounds formulated for release distal to the primary site of iron absorption in the duodenum.

The zinc and/or chelator component is preferably administered together with the supplemental iron, but separate administration of the zinc and/or chelator component, up to about 4 hours, for example up to about 2 hours or up to about 1 hour before or after the supplemental iron, is within the scope of the present method.

Illustrative zinc compounds and complexes and illustrative amounts thereof, where a zinc component is administered, are as set forth hereinabove. Likewise, illustrative ion-chelating compounds, illustrative amounts thereof and illustrative controlled release mechanisms are as set forth hereinabove. In one embodiment of the present method, the zinc and/or chelator component takes the form of a companion composition of the invention as described hereinabove.

The present method is an important contribution to the art because unabsorbed iron in excessive amounts can have adverse, including toxic, effects in the gastrointestinal tract. Since nonheme iron absorption efficiency decreases with increasing dosage, it is at high doses of supplemental iron, above about 0.6 mmol (about 33.5 mg) per day, that unabsorbed iron has the greatest potential to cause such adverse effects.

Without being bound by theory, unabsorbed iron in the gastrointestinal lumen is not constrained by carrier or storage proteins, and is thus "free" iron that can catalyze the formation of injurious compounds. Superoxide ($.O_2^-$) radicals, produced for example during reperfusion following a period of ischemia, and hydrogen peroxide ($H_2O_2$) formed by dismutation of these radicals, may themselves have relatively low cellular oxidative activity. However, in a two-step reaction mediated by iron (the superoxide-driven Fenton reaction), hydroxyl (.OH) radicals can be generated:

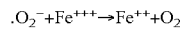

$.O_2^- + Fe^{+++} \rightarrow Fe^{++} + O_2$

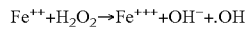

$Fe^{++} + H_2O_2 \rightarrow Fe^{+++} + OH^- + .OH$

These .OH radicals are highly reactive, attacking lipids, proteins and nucleic acids. Peroxidized lipids and proteins can form cross linkages that interfere with or even destroy the normal functions of these compounds and may trigger an inflammatory response. Nucleic acid (including DNA) peroxidation can similarly form cross linkages; these can impair replication and, particularly where oxidative stress is prolonged, result in mutation of proto-oncogenes and tumor suppressor genes, microsatellite instability, chromosomal rearrangement, transcriptional dysregulation and signal transduction and replication, all of which are associated with carcinogenesis.

A positive correlation has been demonstrated between dietary iron and colorectal cancer (CRC) risk. Without being bound by theory, it is believed that increased CRC risk is associated at least in part with iron that remains unabsorbed during passage through the duodenum and remains available for uptake by epithelial cells in the colon. Increased iron staining has been observed in human colorectal tumors, and it is believed that retention of iron by such tumors can facilitate cell proliferation, leading to CRC.

Thus in a particular embodiment, the present method is useful to reduce oxidative stress, and its effects including elevated risk of CRC, associated with doses of supplemental iron of about 0.6 to about 3 mmol per day. Zinc and/or chelator components as provided by the present invention can mitigate such effects, as explained below.

Zinc is well known to interfere with absorption of iron and iron to interfere with absorption of zinc. The transport protein DMT1 (divalent metal transporter 1) binds and transports both $Fe^{++}$ and $Zn^{++}$; hence a competitive antagonism can be explained on the basis that these ions share a common transporter. In the light of the well recognized need to improve or promote the absorption of oral iron, it is therefore counterintuitive to administer zinc with supplemental or therapeutic doses of iron, as proposed by the present invention. This is especially so at doses of supplemental iron of about 0.6 mmol (about 33.5 mg) per day or greater, even more so as daily dose increases to about 40 mg or greater, 50 mg or greater or 60 mg or greater, for example about 60 to about 120 mg, for it is at these higher doses that efficiency of absorption is already reduced. Further inhibiting iron uptake by adding a competitive antagonist such as zinc runs counter to conventional thinking in the art, considering that such inhibition would be expected to result in even greater levels of iron in the distal gastrointestinal tract lumen, with added potential for adverse effects.

Without being bound by theory, it is believed that zinc-containing dosage systems, companion compositions and methods of the present invention provide modulation by zinc with iron absorption in one or more of the following ways:

1. through modulation of bifunctional cytosolic aconitase (IRP1), a key protein of the intracellular signaling pathway, to increase transferrin (iron transport protein) receptor expression on a cell surface to enhance uptake of iron into the cell and simultaneously down-regulate synthesis of ferritin (iron storage protein);
2. through very significant increase in expression of metallothionein at the site of increased iron uptake, a major mechanism by which zinc exerts its antioxidant effect; and
3. through reduction in thiobarbituric acid reactive substances (TBARS) and carbonyl protein levels, which are indicators of oxidative stress.

These benefits of zinc apply both at the site of systemic iron absorption in the duodenum (where the benefits are obtainable only with immediate-release zinc) and at sites of potential local iron absorption or "trapping" in the distal gastrointestinal tract (obtainable with immediate-release or controlled-release zinc).

Accordingly, in a particular embodiment of the invention there is provided a method for mitigating one or more gastrointestinal adverse effects of unabsorbed iron in a human subject, the method comprising orally administering one or more zinc compounds and/or complexes in a total elemental zinc amount effective (i) to inhibit cytosolic and/or mitochondrial aconitase activity and (ii) to increase metallothionein expression in enterocytes of the subject at one or more sites of iron uptake. Without being bound by theory, it is proposed that inhibiting aconitase activity results in increased transferrin receptor activity on the enterocyte membrane and thereby enhances iron uptake from the lumen, thus decreasing the amount of unabsorbed iron distal to the site of uptake. Meanwhile, again without being bound by theory, it is proposed that the increased metallothionein expression provides antioxidant protection against local iron overload. See Bodiga & Krishnapillai (2007) supra.

Ion-chelating compounds such as DFO are used therapeutically to treat systemic iron overload, i.e., in situations where excess iron has been absorbed as opposed to those situations addressed by the present invention, where excessive levels of unabsorbed iron are present in the lumen of the lower gastrointestinal tract. Because DFO (like EDTA) has very poor (typically <5%) oral absorption, it is administered by intravenous or subcutaneous injection for systemic iron overload therapy. According to embodiments of the present invention, by contrast, an ion-chelating compound such as DFO or EDTA is administered orally; being poorly absorbed it remains available in the gastrointestinal lumen to scavenge unabsorbed iron.

However, if an ion-chelating compound is present in significant amount in the duodenal lumen, it can be expected to bind iron there and render it unavailable for the desired absorption at that site. For practice of the present invention, therefore, it is important to provide the ion-chelating compound(s) in a delayed or controlled release formulation, more particularly one that provides minimal release in the duodenum or proximal thereto, but adequate release distal to the duodenum, for example in the jejunum, ileum and colon. As indicated above, this can be achieved by known mechanisms such as enteric coating or other pH-sensitive release mechanisms.

Thus the present invention provides, in part, a combination of components, namely iron and an ion-chelating compound, that has hitherto been contrary to established thinking in the art, but that, when administered in a way that segregates their locus of release in the gastrointestinal tract, more particularly by formulating the ion-chelating compound for release distal to the primary site of iron absorption in the duodenum, gives rise to the benefits set forth herein.

Parameters that can be used to assess efficacy of distal bowel iron chelation can include fecal iron content, fecal ROS (reactive oxidative species) induction, intestinal morphology by endoscopy or biopsy, and clinical symptoms of iron-related gastrointestinal adverse effects, for example constipation, diarrhea and abdominal cramps.

The invention is further illustrated but not limited by the following Examples.

EXAMPLES

In the Examples, iron is used in the form of Iron Taste-Free® (ferric glycinate), Sumalate® (ferrous asparto glycinate) and/or Ferrochel® (ferrous bisglycinate), all of which are products of Albion Laboratories, Inc., each containing approximately 20% by weight elemental iron. Iron-Taste Free®, Sumalate® and Ferrochel® products are presented as either alternatives in the Examples or one or more can be used in combination. It is not to be taken to imply that these products are entirely equivalent to each other.

For example, Sumalate® alone may be present as the iron component in any one of the relevant Examples below or embodiments described herein. Alternatively, a two way combination, such as Sumalate® and Ferrochel® may be present as the iron component in any one of the relevant Examples below or embodiments described herein. Further, a three way combination of Iron-Taste Free®, Sumalate® and Ferrochel® may be present as the iron component in any one of the relevant Examples below or embodiments described herein. Illustratively, each of Iron-Taste Free®, Sumalate® and Ferrochel® can be present in the following ratio, 0-10:0-10:0-10, with a minimum that at least one has to be present.

The dosage systems and compositions exemplified are in the form of tablets, but those of skill in the art, based on the information provided, will readily prepare alternative dosage forms within the scope of the invention. The amounts of ingredients shown are for a single tablet.

The ingredients are dry-blended or granulated and tableted by standard methods of pharmacy. Where DFO (deferoxamine) is shown, it will be understood to be in delayed-release form in accordance with an embodiment of the invention.

Example 1: Dosage System Comprising Iron and Zinc Components

| Ingredient | Amount (mg) | Fe (mg) | Zn (mg) |
| --- | --- | --- | --- |
| Iron Taste-Free ®, Sumalate ®, and/or Ferrochel ® | 250 | 50 | |
| zinc bisglycinate | 243 | | 48 |
| excipients | q.s. | | |

The Zn:Fe molar ratio in the tablet of Example 1 is approximately 0.8:1. Recommended dose is 1-2 tablets daily.

Example 2: Dosage System Comprising Iron and Zinc Components

| Ingredient | Amount (mg) | Fe (mg) | Zn (mg) |
| --- | --- | --- | --- |
| Iron Taste-Free ®, Sumalate ®, and/or Ferrochel ® | 250 | 50 | |
| zinc bisglycinate | 101 | | 20 |
| excipients | q.s. | | |

The Zn:Fe molar ratio in the tablet of Example 2 is approximately 0.33:1. Recommended dose is 1-2 tablets daily.

Example 3: Dosage System Comprising Iron and Zinc Components

| Ingredient | Amount (mg) | Fe (mg) | Zn (mg) |
| --- | --- | --- | --- |
| Iron Taste-Free ®, Sumalate ®, and/or Ferrochel ® | 125 | 25 | |
| zinc bisglycinate | 177 | | 35 |
| excipients | q.s. | | |

The Zn:Fe molar ratio in the tablet of Example 3 is approximately 1.2:1. Recommended dose is 1-2 tablets daily.

Example 4: Dosage System Comprising Iron, Zinc and Chelator Components

| Ingredient | Amount (mg) | Fe (mg) | Zn (mg) |
| --- | --- | --- | --- |
| Iron Taste-Free ®, Sumalate ®, and/or Ferrochel ® | 250 | 50 | |
| zinc bisglycinate | 243 | | 48 |
| DFO | 350 | | |
| excipients | 250 | | |

The Zn:Fe molar ratio in the tablet of Example 4 is approximately 0.8:1. Recommended dose is 1-2 tablets daily.

Example 5: Dosage System Comprising Iron, Zinc and Chelator Components

| Ingredient | Amount (mg) | Fe (mg) | Zn (mg) |
| --- | --- | --- | --- |
| Iron Taste-Free ®, Sumalate ®, and/or Ferrochel ® | 250 | 50 | |
| zinc bisglycinate | 243 | | 48 |
| DFO | 500 | | |
| excipients | 250 | | |

The Zn:Fe molar ratio in the tablet of Example 5 is approximately 0.8:1. Recommended dose is 1-2 tablets daily.

Example 6: Companion Tablet Comprising Zinc and Chelator Components

| Ingredient | Amount (mg) | Zn (mg) |
| --- | --- | --- |
| zinc bisglycinate | 250 | 50 |
| DFO | 500 | |
| excipients | 250 | |

The companion tablet of Example 6 is designed for co-administration with an iron supplement. When administered with 50 mg iron, Zn:Fe molar ratio provided by the companion tablet of Example 6 is approximately 0.8:1. Recommended dose is 1 companion tablet per 50 mg supplemental iron.

Example 7: Dosage System Comprising Iron and Chelator Components

| Ingredient | Amount (mg) | Fe (mg) |
| --- | --- | --- |
| Iron Taste-Free ®, Sumalate ®, and/or Ferrochel ® | 250 | 50 |
| DFO | 500 | |
| excipients | 250 | |

Recommended dose is 1-2 tablets daily.

Example 8: Companion Tablet Comprising Chelator Component

| Ingredient | Amount (mg) |
| --- | --- |
| DFO | 500 |
| excipients | 250 |

The companion tablet of Example 8 is designed for co-administration with an iron supplement. Recommended dose is 1 companion tablet per 50 mg supplemental iron.

Example 9: Companion Tablet Comprising Zinc and Chelator Components

| Ingredient | Amount (mg) | Zn (mg) |
| --- | --- | --- |
| zinc bisglycinate | 250 | 50 |
| copper | 1 | |
| DFO | 500 | |
| excipients | 250 | |

The companion tablet of Example 9 is designed for co-administration with an iron supplement. When administered with 50 mg iron, Zn:Fe molar ratio provided by the companion tablet of Example 9 is approximately 0.8:1. Recommended dose is 1 companion tablet per 50 mg supplemental iron.

What is claimed is:

1. An orally deliverable dosage system for supplementing iron nutrition comprising
   (a) iron in a form of one or more physiologically acceptable iron grades, compounds and/or complexes, in a total elemental iron amount of about 0.6 to about 3 mmol, wherein the iron is not in a controlled release form; and
   (b) an agent to mitigate one or more gastrointestinal adverse effects of unabsorbed iron, said agent comprising an ion-chelating compound formulated for release distal to the primary site of iron absorption in the duodenum, wherein the ion-chelating compound is not complexed with iron;
   wherein the dosage system is an iron supplement in a form of a single composition containing said iron and said mitigating agent, or in a form of an iron-containing composition and a companion composition containing the mitigating agent.
2. The dosage system of claim 1, wherein the ion-chelating compound is chosen from DFO (deferoxamine), ethylene diamine tetraacetic acid (EDTA), deferiprone, or deferasiro.

3. The dosage system of claim 1, wherein said dosage system comprises a form of iron selected from ferrous asparto glycinate, ferrous bisglycinate, ferric glycinate, ferrous aspartate, and ferrous histidinate.

4. The dosage system of claim 1, wherein said dosage system is a nonfood dosage system.

5. The dosage system of claim 1, wherein the mitigating agent further comprises one or more physiologically acceptable zinc compounds and/or complexes, in a total elemental zinc amount of about 0.1 to about 1.2 mmol per mmol iron, optionally formulated for release of the one or more zinc compounds and/or complexes distal to the primary site of iron absorption in the duodenum.

6. A method for supplementing iron nutrition in a human subject in need thereof, comprising orally administering the dosage system of claim 1.

7. The dosage system of claim 1, wherein the zinc is provided as zinc arginate, zinc aspartate, zinc bisglycinate, citrated zinc bisglycinate, or zinc histidinate.

8. The dosage system of claim 1, wherein the dosage system is an iron supplement in a form of a single composition containing said iron and said mitigating agent.

9. An oral supplement in a single discrete dosage form, wherein the dosage form comprises:
   (a) an iron-containing composition comprising iron in a form of one or more compounds and/or complexes, physiologically acceptable grades of iron, in an amount of total elemental iron from about 0.06 to about 3 mmol, wherein the iron-containing composition is not in a controlled release form; and
   (b) a companion composition comprising an ion-chelating compound in a time or pH-triggered, controlled release form for release of the ion-chelating compound distal to the primary site of iron absorption in the duodenum, wherein the ion-chelating compound is not complexed with iron.

10. The oral supplement in a single discrete dosage form of claim 9, wherein the ion-chelating compound is in the form of an apochelator.

11. The dosage system of claim 1, wherein the ion-chelating compound is in the form of an apochelator.

* * * * *